| United States Patent [19] | [11] Patent Number: 4,551,534 |
| Sulkowski et al. | [45] Date of Patent: Nov. 5, 1985 |

[54] ARALKYL OR ARYLOXYALKYL 1,7-NAPHTHYRIDINE-3-CARBOXYLIC ACID ESTERS

[75] Inventors: Theodore S. Sulkowski, Wayne; Paul J. Silver, West Chester; Albert A. Mascitti, Norristown; Reinhold H. W. Bender, Valley Forge, all of Pa.

[73] Assignee: American Home Products Corporation, New York, N.Y.

[21] Appl. No.: 595,168

[22] Filed: Mar. 30, 1984

[51] Int. Cl.[4] ............................................. C07D 471/02
[52] U.S. Cl. ................................. 546/123; 544/127; 544/362
[58] Field of Search ................. 544/127, 362; 546/123

[56] References Cited

U.S. PATENT DOCUMENTS 4,321,384  3/1982  Sulkowski et al. ................. 546/123
4,365,063  12/1982  Sulkowski et al. ................. 546/123

OTHER PUBLICATIONS

Nayler et al., Basic Res. Cardiol., 76, 1–15, (1981).
Saida et al., Circulation Research, 52, No. 2, 137–142, (1983).
Daly et al., European J. of Pharmacology, 90, 103–108, (1983).
"Medicinal Chemistry", Alfred Burger, ed., 3rd ed., Wiley–Interscience, 1970.

Primary Examiner—Henry R. Jiles
Assistant Examiner—Barbara Cassatt
Attorney, Agent, or Firm—Richard K. Jackson

[57] ABSTRACT

7-(Substituted)-1,4,5,6,7,8-hexahydro-2-alkyl-4-aryl-5-oxo-1,7-naphthyridine-3-carboxylic acid esters and pharmaceutically acceptable acid addition salts thereof are useful antihypertensive agents.

13 Claims, No Drawings

ARALKYL OR ARYLOXYALKYL 1,7-NAPHTHYRIDINE-3-CARBOXYLIC ACID ESTERS

BACKGROUND OF THE INVENTION

Pharmacological agents possessing the ability to block cellular transmembrane influx of calcium are capable of suppressing that portion of myocardial or vascular smooth muscle contractility which is dependent upon extracellular calcium. Church et al., Can. J. Physiol. Pharmacol., 58, 254 (1980); Fleckenstein, Calcium and the Heart, P. Harris and L. Opie, eds., Academic Press (1971); Nayler et al., Bas. Res. Cardiol., 76, 1 (1981); Calcium Blockers, S. Flaim and R. Zelis, eds., Urban and Schwartzenberg, (1982).

These pharmacological agents, termed calcium entry blockers, have been proven to be useful in the treatment of hypertension, cardiac arrhythmias, angina pectoris, and coronary artery vasospasm (a possible cause of sudden cardiac death syndrome). Circ. Res., 52, Suppl. I, (1983); Hypertension 5, Suppl. II, (1983). However, a major limitation and deleterious side-effect for use of some of these agents in certain vascular pathologies is the negative inotropism associated with blockade of cardiac sarcolemmal $Ca^{+2}$ channels.

In theory, calcium entry blockers are thought to act by blocking calcium influx through discrete calcium channels (slow channels) in cell membranes. Various tissues exhibit relative differences in sensitivity toward the calcium blocking effect achieved by certain calcium antagonists, theoretically as a result of tissue specific differences in the calcium channels. Acta Pharmacol. Toxicol., 43, 5 (1978); loc. cit. 291 (1978); Microvascular Res., 5, 73 (1973); Am. Rev. Pharmacol. Toxicol., 17, 149 (1977).

A mechanistic difference in $Ca^{+2}$ regulation of contractile activity in vascular smooth muscle and cardiac muscle is believed to exist. In cardiac muscle, $Ca^{+2}$ regulation is primarily thin filament-linked and involves the troponin-tropomyosin system. Stull et al., Handbook of Physiology, The Cardiovascular System, vol. 1, R. Berne, N. Sperelakis and S. Geiger, eds., American Physiological Society (1979); Solaro, Calcium Blockers, ibid., supra. In vascular smooth muscle, regulation is primarily dependent upon $Ca^{+2}$-calmodulin mediated myosin light chain phosphorylation. Hartshorne et al., Handbook of Physiology, The Cardiovascular System, vol. 2., Bohr, Somlyo and Sparks, eds., American Physiological Society (1982); Silver et al., Calcium Blockers, ibid., supra.

Calcium antagonists which are more specific for vascular smooth muscle than cardiac muscle would be less liable to produce negative inotropic cardiac contraction.

DESCRIPTION OF THE INVENTION

In accordance with this invention there is provided a group of 7-substituted-1,4,5,6,7,8-hexahydro-2-alkyl-4-aryl-5-oxo-1,7-naphthyridine-3-carboxylic acid esters and pharmaceutically acceptable acid addition salts thereof, which are useful antihypertensive agents.

More specifically, the antihypertensive agents of this invention are compounds of the formula

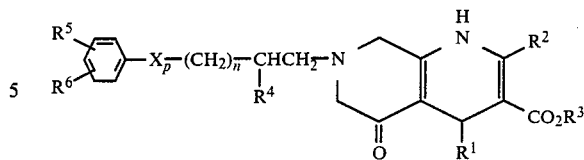

in which
$R^1$ is tetra- or penta- chloro, bromo or fluoro- phenyl or

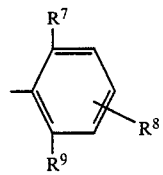

where $R^7$ and $R^9$ are, independently, hydrogen, alkyl of 1 to 6 carbon atoms, halo, trifluoromethyl, alkoxy of 1 to 6 carbon atoms, alkylthio of 1 to 6 carbon atoms, cyano or nitro and $R^8$ is hydrogen, alkyl of 1 to 6 carbon atoms, halo, trifluoromethyl, cyano or nitro;

$R^2$ is alkyl of 1 to 6 carbon atoms;

$R^3$ is alkyl of 1 to 6 carbon atoms, alkoxyalkyl in which each alkyl moiety is of 1 to 6 carbon atoms, $-CH_2CF_3$, $-CH_2CH_2CF_3$ or

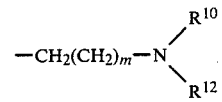

where $R^{10}$ is hydrogen or alkyl of 1 to 6 carbon atoms; and $R^{12}$ is alkyl of 1 to 6 carbon atoms or arylalkyl of 7 to 10 carbon atoms, and $R^{10}$ and $R^{12}$, taken with the nitrogen atom to which they are attached, form a pyrrolidinyl, imidazolidinyl, piperidyl, piperazinyl, 4-alkylpiperazinyl, in which the alkyl group contains from 1 to 6 carbon atoms, or morpholinyl heterocycle; and m is one of the integers 0, 1 or 2;

$R^4$ is hydrogen, hydroxy or alkyl of 1 to 3 carbon atoms;

$R^5$ and $R^6$ are, independently, hydrogen, $-Cl$, $-Br$, $-F$, trifluoromethyl, alkyl of 1 to 6 carbon atoms or alkoxy of 1 to 6 carbon atoms;

X is $-O-$, or $-S-$;

n is one of the integers 0, 1, 2 or 3; and p is one of the integers 0 or 1, with the proviso that when n is 0, p is 0 and $R^4$ is hydroxy;

or a pharmaceutically acceptable salt thereof.

With reference to the above-described genus of compounds, the preferred variables from the standpoint of production economics and activity profile are those in which the group $R^1$ contains halogen substituents, more preferably fluoro substituents, $R^3$ is alkyl of 1 to 3 carbon atoms, $R^4$ is hydroxyl, and when p is 1, X is O and n is 1, and when p is 0, n is 2.

The compounds of this invention may be prepared by reaction of equimolar quantities of an appropriately substituted hexahydro-2-alkyl-4-aryl-5-oxo-1,7-naphthyridine-3-carboxylic acid ester (disclosed or prepared by methods disclosed in U.S. Pat. Nos. 4,321,384 and 4,365,063) and an alkylating reactant such as an epoxide of the formula

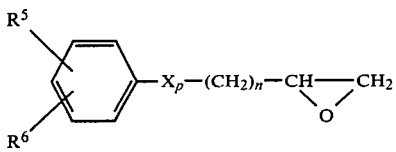

where $R^5$, $R^6$, X, p and n have the definitions disclosed above, with which the alkylation is carried out at elevated temperature (reflux) in a lower alkanol (methanol, ethanol, isopropanol, etc.) for a period from about 4 to about 18 hours, or an alkylhalide of the formula

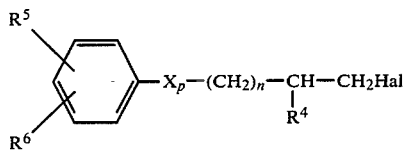

where $R^5$, $R^6$, X, p and n are described above, $R^4$ is hydrogen or alkyl of 1 to 6 carbon atoms and Hal is chlorine or bromine, where the reaction is conducted at elevated temperature (reflux) in a lower alkanol (n-butanol, ethanol, propanol, etc.) in the presence of a base ($K_2CO_3$, $Na_2CO_3$, etc.) for a period of from about 6 to about 24 hours. The epoxide or halide reactants are either known literature compounds or are readily prepared by techniques well within the skill of the medicinal chemist.

The pharmaceutically acceptable salts of the antihypertensive agents of this invention are prepared directly by neutralization of the free base or by methathetical displacement. The physiologically acceptable salts may be formed with organic or inorganic acids such as hydrochloric, hydrobromic, phosphoric, sulfuric, sulfonic, nitric, methylsulfonic, acetic, maleic, succinic, fumaric, tartaric, citric, salicylic, lactic, naphthalenesulfonic acid, and the like.

The compounds of this invention were initially shown to exhibit $Ca^{+2}$ antagonism in rabbit aortic smooth muscle following a modified procedure from that describe by Brockaert el al., Eur. J. Pharmacol., 53, 281 (1979) whereby transverse strips (10 mm × 2.5 mm), from the thoracic aorta were cut and suspended vertically in a jacketed (37° C.-50 ml volume) organ bath in physiological saline solution (PSS) aerated with 95% $O_2$/5% $CO_2$. The composition of PSS was as follows (mM): NaCl 112, KCl 5, $NaHCO_3$ 25, $KH_2PO_4$ 1, $MgSO_4$ 1.2, $CaCL_2$ 2.5, dextrose 10. The lower end of each tissue strip was attached to a fixed post and the upper end to a Statham UC-4 transducer. Changes in force development were recorded on a Beckman Dynograph Polygraphic Recorder.

Following equilibration, the muscles were contracted in a depolarizing solution of PSS in which 100 mM KCl was substituted for an equimolar concentration of NaCl. Following attainment of steady-state isometric force (20 min.), the test compound was added to afford a final concentration of $1 \times 10^{-5}M$. The inhibitory effect, expressed as percent relaxation, was determined from the mean of two experiments twenty minutes after the addition of the compound being tested.

The hypotensive in vivo effect of the compounds of this invention was determined by measuring changes in the systolic blood pressure of spontaneously hypertensive rats with a Decker Caudal Plethysmograph. The compound being tested was administered to a group of 4 rats and their systolic pressure was determined prior to and at 1.5 and 4 hours after compound administration. Initial testing was done by oral administration of the compound at a dose of 50 mg/kg body weight. Results (mmHg) are expressed as decreases in systolic blood pressure.

The potential for detrimental cardiac depressant (negative inotropic) effects of the compounds of this invention was assessed in isolated paced intact rabbit atria. Left and right atria (with nodal tissue excised) were suspended vertically in a jacketed (30° C.) organ bath containing 50 ml of PSS and aerated with 95% $O_2$/5% $CO_2$. Muscles (N=5-9/compound) were stimulated at a frequency of 3 Hz with a WPI stimulator for a 60 minute equilibration period. Changes in isometric force were recorded as described for the aortic smooth muscle experiments, supra. Following equilibration, the test compound (or as a standard, the ethanol vehicle) was added to the organ bath in a cumulative manner from doses ranging from $10^{-9}M$ to $10^{-5}M$ ($10^{-5}M$ was the maximum dose which could be attained due to the depressant effect of ethanol) and effects on developed isometric force were determined. Results are expressed as the concentration of calcium antagonist which produces 25% inhibition of isometric force ($IC_{25}$).

Known calcium entry blockers produced significant cardiac depression in this model. Verapamil ($IC_{25}=6\times10^{-8}M$), nifedipine ($IC_{25}=5\times10^{-8}M$), nitrendipine ($IC_{25}=3.5\times10^{-7}M$) and felodipine ($IC_{25}=8\times10^{-7}M$) all produced direct negative inotropism. However, the known calmodulin inhibitor, W-7, produced less than 20% inhibition at the highest concentration ($10^{-5}M$) tested.

Thus, these data establish the compounds of this invention as $Ca^{30\ 2}$ antagonists which are useful as antihypertensive agents functioning more at the vascular level than other known $Ca^{+2}$ entry blockers. It has been observed that compounds of this invention inhibit arterial $Ca^{+2}$-calmodulin dependent myosin light chain phosphorylation and subsequent contractile protein function.

Based upon the activity profile elicited by the compounds of this invention in the above-described standard scientifically recognized test models, the compounds are established as hypotensive agents useful in the treatment of hypertension and conditions characterized by constrictive blood flow in coronary arteries. For that purpose, the compounds may be administered orally or parenterally in suitable dosage forms compatable with the route of administration, whether oral, intraperitoneal, intramuscular, intravenous, intranasal, buccal, etc. The effective dose range determined in the animal test models has been established at from 1 to about 50 milligrams per kilogram host body weight to be administered in single or plural doses as needed to obtain the desired hypotensive response. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose (e.g. from about 25 milligrams to about 4 grams) of the active ingredient alone or in combination with adjuvants needed for conventional coating, tableting, solubilizing, flavor or coloring. Parenteral administration with liquid unit dosage forms may be via sterile solutions or suspensions in aqueous or oleagenous medium. Isotonic aqueous vehicle for injection is preferred with or without stabilizers, preservatives and emulsifiers.

The following examples illustrate the preparation of a representative number of compounds of this invention. After each example, the $Ca^{+2}$ antagonist activity of the compound is presented in terms of percent relaxation (P.R.) at $10^{-5}M$ concentration unless indicated otherwise. Similarly, the antihypertensive activity is reported in terms of millimeters mercury (mmHg) blood pressure (B.P.) reduction at the stated time post 50 mg/kg oral dosing or other dosing as indicated. Also, the $IC_{25}$ data, where determined, is presented for comparison purposes with that of standard $Ca^{+2}$ antagonists noted, supra, and to show that the compounds of this invention are operating more through the vascular smooth muscle regulatory mechanism than the known $Ca^{+2}$ entry blockers.

EXAMPLE 1

7-[3-(2,3-Dimethylphenoxy)-2-hydroxypropyl]-1,4,5,6,7,8-hexahydro-2-methyl-4-(2-methylphenyl)-5-oxo-1,7-naphthyridine-3-carboxylic acid methyl ester 1,4,5,6,7,8-Hexahydro-2-methyl-4-(2-methylphenyl)-5-oxo-1,7-naphthyridine-3-carboxylic acid methyl ester (14.5 g), 6.8 g of 3-(2,3-dimethylphenoxy)-1,2-epoxypropane and 250 ml of methanol were combined and refluxed for 18 hours. The solvent was removed in vacuo. The residue was dissolved in diethyl ether and saturated with hydrogen chloride. The solid was separated and dried in vacuo at 75° C. for 18 hours. The solid was recrystallized from acetonitrile to obtain 7.7 g of the title compound as the hydrochloride salt, m.p. 220° C. dec.

Analysis for: $C_{29}H_{36}N_2O_5 \cdot HCl$. Calculated: C, 66.08; H, 6.69; N, 5.31; Cl, 6.73. Found: C, 65.46; H, 6.63; N, 5.21; Cl, 6.69.

P.R.=91.
$IC_{25} > 1 \times 10^{-5}M$.
B.P.=−30 at 1.5 hours; −34 at 4 hours.

EXAMPLE 2

7-[3-(2,3-Dimethylphenoxy)-2-hydroxypropyl]-1,4,5,6,7,8-hexahydro-2-methyl-5-oxo-4-(pentafluorophenyl)-1,7-naphthyridine-3-carboxylic acid methyl ester 1,4,5,6,7,8,-Hexahydro-2-methyl-5-oxo-4-(2,3,4,5,6-pentafluorophenyl)-1,7-naphthyridine-3-carboxylic acid methyl ester (14 g), 6.4 g of 3-(2,3-dimethylphenoxy)-1,2-epoxypropane and 250 ml of methanol were refluxed for 18 hours. The solvent was removed in vacuo and the residue was dissolved in diethyl ether. After standing at room temperature for two days, the solid was separated and washed with diethyl ether to obtain 13.6 g of product, m.p. 161°-3° C.

The solid was dissolved in methanol and saturated with hydrogen chloride. The solution was evaporated to dryness in vacuo. The residue was solidified by trituration with diethyl ether. On recrystallization from acetonitrile there was obtained the title compound as the hydrochloride salt, m.p. 228°-230° C. dec.

Analysis for: $C_{28}H_{27}N_2O_5F_5 \cdot HCl$. Calculated: C, 55.77; H, 4.68; N, 4.64; Cl, 5.88. Found: C, 55.86; H, 4.60; N, 5.01; Cl, 5.99.

P.R.=65.
$IC_{25} = 5 \times 10^{-6}M$.
B.P.=−56 at 1.5 hours; −86 at 4 hours; −28 at 24 hours.

EXAMPLE 3

7-[3-(2,3-Dimethylphenoxy)-2-hydroxypropyl]-1,4,5,6,7,8-hexahydro-5-oxo-4-(2,3,5,6-tetrafluorophenyl)-1,7-naphthyridine-3-carboxylic acid methyl ester A solution of 7.26 g of 1,4,5,6,7,8-hexahydro-2-methyl-5-oxo-4-(2,3,5,6-tetrafluorophenyl)-1,7-naphthyridine-3-carboxylic acid methyl ester, 3.50 g of 3-(2,3-dimethylphenoxy)-1,2-epoxypropane and 200 ml of methanol was refluxed for 8 hours. The solvent was removed in vacuo and the residue was crystallized from ethyl acetate. The solid was separated and dried in vacuo to obtain 6.5 g of product, m.p. 200°-202° C. dec.

The solid was dissolved in ethanol and treated with excess hydrogen chloride. The solvent was evaporated in vacuo. The residue was dissolved in hot ethyl acetate and diluted with diethyl ether. After stirring several hours, the solid was separated by filtration. Recrystallization from ethanol-diethyl ether afforded the title compound as the hydrochloride salt, m.p. 215°-220° C. dec.

Analysis for: $C_{28}H_{28}N_2O_3F_4 \cdot HCl$. Calculated: C, 57.49; H, 5.00; N, 4.79; Cl, 6.06. Found: C, 57.25; H, 4.91; N, 4.79; Cl, 5.82.

P.R.=63
$IC_{25} = 6 \times 10^{-6}M$
B.P.=−25 at 1.5 hours; −56 at 4 hours.

EXAMPLE 4

4-(2,3-Dichloro-6-fluorophenyl)-7-[3-(2,3-dimethylphenoxy)-2-hydroxypropyl]1,4,5,6,7,8-hexahydro-2-methyl-5-oxo-1,7-naphthyridine-3-carboxylic acid methyl ester 4-(2,3-Dichloro-6-fluorophenyl)-1,4,5,6,7,8-hexahydro-2-methyl-5-oxo-1,7-naphthyridine-3-carboxylic acid methyl ester (12.1 g), 5.3 g of 3-(2,3-dimethylphenoxy)-1,2-epoxypropane and 150 ml of methanol were combined and refluxed for 18 hours. The alcohol was evaporated in vacuo. The residue was chromatographed on silica-gel using a 5% methanol-ethyl acetate system. The residue obtained on evaporation was dissolved in methanol and saturated with hydrogen chloride. The solvent was removed in vacuo and the residue was dissolved in ethyl acetate. A precipitate formed on standing at room temperature. The solid was separated and treated with boiling acetonitrile. The solid was dried in vacuo to obtain 2.8 g of the title compound as the hydrochloride salt, m.p. 190°-3° C.

Analysis for: $C_{28}H_{29}N_2Cl_2FO_5 \cdot HCl$. Calculated: C, 56.06; H, 5.04; N, 4,67; Cl, 17.73. Found: C, 55.94; H, 4.94; N, 4.64; Cl, 17.47.

P.R.=42.
$IC_{25} > 1 \times 10^{-5}M$.
B.P.=−56 at 1.5 hours; −72 at 4 hours.

EXAMPLE 5

7-[3-(2,3-Dichlorophenoxy)-2-hydroxypropyl]-1,4,5,6,7,8-hexahydro-2-methyl-4-(2-methylphenyl)-5-oxo-1,7-naphthyridine-3-carboxylic acid methyl ester 1,4,5,6,7,8-Hexahydro-2-methyl-4-(2-methylphenyl)-5-oxo-1,7-naphthyridine-3-carboxylic acid methyl ester (6.0 g), 4.5 g of 3-(2,3-dichlorophenoxy)-1,2-epoxypropane and 150 ml of methanol were combined and refluxed for five hours. The solvent was evaporated in vacuo. The residue was triturated with diethyl ether and filtered to obtain 6 g of product, m.p. 198°–201° C. The solid was suspended in methanol and saturated with hydrogen chloride. The solution was filtered and evaporated to dryness in vacuo. The residue was recrystallized from acetonitrile to obtain the title compound as the hydrochloride salt, m.p. 207°–209° C. dec.

Analysis for: $C_{27}H_{28}N_2Cl_2O_5 \cdot HCl$. Calculated: C, 57.10; H, 5.15; N; 4.93; Cl, 18.73. Found: C, 57.00; H, 5.06; N, 4.90; Cl, 18.31.

P.R.=62.

$IC_{25} > 1 \times 10^{-5}$M.

B.P.= −23 at 1.5 hours; −25 at 4 hours.

EXAMPLE 6

1,4,5,6,7,8-Hexahydro-2-methyl-5-oxo-4-(pentafluorophenyl)-7-(3-phenoxy-2-hydroxypropyl)-1,7-naphthyridine-3-carboxylic acid methyl ester 1,4,5,6,7,8-Hexahydro-2-methyl-5-oxo-4-(2,3,4,5,6-pentafluorophenyl)-1,7-naphthyridine-3-carboxylic acid methyl ester (7 g), 3 g of 1,2-epoxy-3-phenoxypropane and 125 ml of methanol were combined and refluxed for 18 hours. The solvent was removed in vacuo and the residue solidified on cooling. The solid was recrystallized from ethyl acetate-hexane to obtain 7 g of product, m.p. 168°–170° C.

The solid was dissolved in methanol and saturated with hydrogen chloride. The solvent was removed in vacuo and the residue was crystallized from ethyl acetate. Recrystallization from acetonitrile afforded the title compound as the hydrochloride salt, m.p. 230° C. dec.

Analysis for: $C_{26}H_{23}N_2F_5O_5 \cdot HCl$. Calculated: C, 54.31; H, 4.21; N, 4.87; Cl, 6.17. Found: C, 54.40; H, 4.25; N, 4.91; Cl, 6.23.

P.R.=67

$IC_{25} = 4.5 \times 10^{-6}$M

B.P.= −54 at 1.5 hours; −80 at 4 hours.

EXAMPLE 7

1,4,5,6,7,8-Hexahydro-7-[3-(4-methoxyphenoxy)-2-hydroxypropyl]-2-methyl-5-oxo-4-(pentafluorophenyl)-1,7-naphthyridine-3-carboxylic acid methyl ester 1,4,5,6,7,8-Hexahydro-2-methyl-5-oxo-4-(2,3,4,5,6-pentafluorophenyl)-1,7-naphthyridine-3-carboxylic acid methyl ester (5.0 g), 2.3 g of 1,2-epoxy-3-(4-methoxyphenoxy)propane and 125 ml of methanol were combined and refluxed for 18 hours. The solution was saturated with hydrogen chloride, then the methanol was evaporated in vacuo. The residue was crystallized from ethyl acetate. Recrystallization from acetonitrile afforded 4 g of the title compound as the hydrochloride, salt, m.p. 222° C. dec.

Analysis for: $C_{27}H_{25}N_2F_5O_6 \cdot HCl$. Calculated: C, 53.60; H, 4.33; N, 4.63; Cl, 5.86. Found: C, 53.85; H, 4.35; N, 4.72; Cl, 5.65.

P.R.=73

$IC_{25} = 5 \times 10^{-6}$M

B.P.= −31 at 1.5 hours; −56 at 4 hours.

EXAMPLE 8

4-(2,3-Dichlorophenyl)-7-[3-(2,3-dimethylphenoxy)-2-hydroxypropyl]-1,4,5,6,7,8-hexahydro-2-methyl-5-oxo-1,7-naphthyridine-3-carboxylic acid methyl ester A solution of 8.0 g of 4-(2,3-dichlorophenyl)-1,4,5,6,7,8-hexahydro-2-methyl-5-oxo-1,7-naphthyridine-3-carboxylic acid methyl ester, 3.9 g of 3-(2,3-dimethylphenoxy)-1,2-epoxypropane and 100 ml of methanol was refluxed for 16 hours. The solution was cooled in an ice bath, then filtered to obtain 6 g of product, m.p. 210°–214° C. dec. The solid was dissolved in ethanol and treated with excess ethanolic hydrogen chloride. The solution was treated with charcoal, filtered than evaporated to dryness in vacuo. The residue was dissolved in acetonitrile, diluted with diethyl ether and stirred at room temperature for several hours. The solid was separated and recrystallized from acetonitrile-diethyl ether to obtain 3.5 g of the title compound as the hydrochloride salt, m.p. 210°–215° C. dec.

Analysis for: $C_{28}H_{30}N_2Cl_2O_5 \cdot HCl$. Calculated: C, 57.79; H, 5.37; N, 4.82; Cl, 18.28. Found: C, 57.43; H, 5.30; N, 4.75; Cl, 18.10.

P.R.=50.

$IC_{25} = 7 \times 10^{-6}$M.

B.P.= −16 at 1.5 hours; −41 at 4 hours.

EXAMPLE 9

1,4,5,6,7,8-Hexahydro-2-methyl-5-oxo-4-(pentafluorophenyl)-7-(3-phenoxypropyl)-1,7-naphthyridine-3-carboxylic acid methyl ester A mixture of 10 g of 1,4,5,6,7,8-hexahydro-2-methyl-5-oxo-4-(2,3,4,5,6-pentafluorophenyl)-1,7-naphthyridine-3-carboxylic acid methyl ester, 5.6 g of 3-phenoxypropylbromide, 10 g of sodium carbonate and 175 ml of n-butanol was stirred and refluxed for 18 hours. The mixture was filtered and the filtrate was evaporated to dryness. The residue was dissolved in ethyl acetate and extracted with water. After drying over magnesium sulfate, the ethyl acetate was removed in vacuo. The residue was dissolved in methanol and saturated with hydrogen chloride. The solvent was evaporated in vacuo. The residue was dissolved in ethyl acetate and left at room temperature for 18 hours. The solid was separated and recrystallized from ethanolether. A second recrystallization from methanol afforded 2.8 g of the title compound as the hydrochloride salt, m.p. 205° C. dec.

Analysis for: $C_{26}H_{23}N_2F_5O_4 \cdot HCl$. Calculated: C, 55.87; H, 4.33; N, 5.01; Cl, 6.34. Found: C, 55.43; H, 4.30; N, 4.84; Cl, 6.17.

P.R.=61

$IC_{25} = 3.5 \times 10^{-6}$M

B.P.= −43 at 1.5 hours; −41 at 4 hours.

EXAMPLE 10

1,4,5,6,7,8-Hexahydro-7-(2-hydroxy-4-phenylbutyl)-2-methyl-5-oxo-4-(pentafluorophenyl)-1,7-naphthyridine-3-carboxylic acid methyl ester 1,4,5,6,7,8-Hexahydro-2-methyl-5-oxo-4-pentafluorophenyl)-1,7-naphthyridine-3-carboxylic acid methyl ester (10 g), 3.82 g of 1,2-epoxy-4-phenylbutane and 125 ml of methanol were refluxed for 16 hours. The solvent was removed in vacuo. The residue was triturated with ethanol and the resulting solid was separated by filtration. Recrystallization from ethanol afforded 4.2 g of product, m.p. 229°–232° C. dec. The solid was dissolved in ethanol and treated with ethanolic hydrogen chloride. The solution was filtered and evaporated to dryness in vacuo. The residue was recrystallized from methanol-diethyl ether to obtain 2.9 g of the title compound as the hydrochloride salt, m.p. 220°–223° C. dec.

Analysis for: $C_{27}H_{25}N_2F_5O_4 \cdot HCl$. Calculated: C, 56.60; H, 4.57; N, 3.89; Cl, 6.19. Found: C, 56.29; H, 4.48; N, 4.61; Cl, 6.13.

P.R.=80.5
$IC_{25} = 3 \times 10^{-6} M$
B.P.= −41 at 1.5 hours; −51 at 4 hours.

EXAMPLE 11

1,4,5,6,7,8-Hexahydro-7-(2-hydroxy-2-phenylethyl)-2-methyl-5-oxo-4-pentafluorophenyl-1,7-naphthyridine-3-carboxylic acid methyl ester A solution of 7 g of 1,4,5,6,7,8-hexahydro-2-methyl-5-oxo-4-pentafluorophenyl-1,7-naphthyridine-3-carboxylic acid methyl ester, 2.1 g of 1,2-epoxyethylbenzene and 150 ml of methanol was refluxed for 18 hours. The solvent was removed in vacuo and the residue was treated with methanolic hydrogen chloride. The solution was evaporated in vacuo and the residue was covered with diethyl ether and left at room temperature overnight. The diethyl ether was decanted and replaced with ethyl acetate. The residue crystallized after several days. The solid was separated and dried to obtain the title compound as the hydrochloride salt, m.p. 244°–245° C. dec.

Analysis for: $C_{25}H_{21}N_2F_5O_4 \cdot HCl$. Calculated: C, 55.10; H, 4.07; N, 5.14; Cl, 6.51. Found: C, 55.27; H, 4.24; N, 4.91; Cl, 6.45.

P.R.=66.5.
B.P.= −58 at 1.5 hours; −73 at 4 hours.

What is claimed is:

1. A compound of the formula:

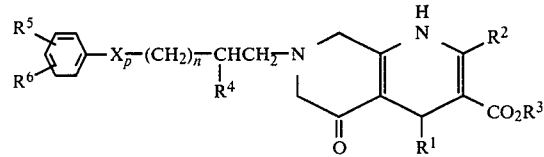

in which $R^1$ is tetra- or penta- chloro, bromo or fluoro- phenyl or

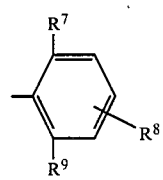

where $R^7$ and $R^9$ are, independently, hydrogen, alkyl of 1 to 6 carbon atoms, halo, trifluoromethyl, alkoxy of 1 to 6 carbon atoms, alkylthio of 1 to 6 carbon atoms, cyano or nitro and $R^8$ is hydrogen, alkyl of 1 to 6 carbon atoms, halo, trifluoromethyl, cyano or nitro;

$R^2$ is alkyl of 1 to 6 carbon atoms;

$R^3$ is alkyl of 1 to 6 carbon atoms, alkoxyalkyl in which each alkyl moiety is of 1 to 6 carbon atoms, —$CH_2CF_3$, —$CH_2CH_2CF_3$ or

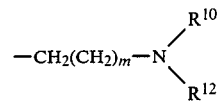

where $R^{10}$ is hydrogen or alkyl of 1 to 6 carbon atoms; and $R^{12}$ is alkyl of 1 to 6 carbon atoms or arylalkyl of 7 to 10 carbon atoms, and $R^{10}$ and $R^{12}$, taken with the nitrogen atom to which they are attached, form a pyrrolidinyl, imidazolidinyl, piperidyl, piperazinyl, 4-alkylpiperazinyl, in which the alkyl group contains from 1 to 6 carbon atoms, or morpholinyl heterocycle; and m is one of the integers 0, 1 or 2;

$R^4$ is hydrogen, hydroxy or alkyl of 1 to 3 carbon atoms;

$R^5$ and $R^6$ are, independently, hydrogen, —Cl, —Br, —F, trifluoromethyl, alkyl of 1 to 6 carbon atoms or alkoxy of 1 to 6 carbon atoms;

X is —O—, or —S—, n is one of the integers 0, 1, 2 or 3; and p is one of the integers 0 or 1, with the proviso that when n is 0, p is 0 and $R^4$ is hydroxy;

or a pharmaceutically acceptable salt thereof.

2. A compound of the formula:

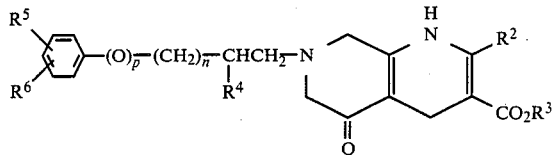

in which $R^1$ is tetra- or penta- chloro, bromo or fluoro- phenyl or

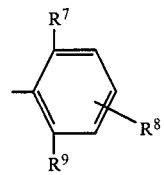

where $R^7$, $R^8$ and $R^9$ are hydrogen or halo; with at least one of $R^7$, $R^8$ and $R^9$ being halo;

$R^2$ is alkyl of 1 to 6 carbon atoms;

$R^3$ is alkyl of 1 to 3 carbon atoms;

$R^4$ is hydroxyl;

$R^5$ and $R^6$ are, independently, hydrogen, —Cl, —Br, —F, trifluoromethyl, alkyl of 1 to 6 carbon atoms or alkoxy of 1 to 6 carbon atoms;

n is one of the integers 1 or 2; and p is one of the integers 0 or 1; with the proviso that when p is 1, n is 1; and when p is 0, n is 2;

or a pharmaceutically acceptable salt thereof.

3. A compound of claim 1 which is 7-[3-(2,3-dimethylphenoxy)-2-hydroxypropyl]-1,4,5,6,7,8-hexahydro-2-methyl-4-(2-methylphenyl)-5-oxo-1,7-naphthyridine-3-carboxylic acid methyl ester or a pharmaceutically acceptable salt thereof.

4. A compound of claim 2 which is 7-[3-(2,3-dimethylphenoxy)-2-hydroxypropyl]-1,4,5,6,7,8-hexahydro-2-methyl-5-oxo-4-(pentafluorophenyl)-1,7-naphthyridine-3-carboxylic acid methyl ester or a pharmaceutically acceptable salt thereof.

5. A compound of claim 2 which is 7-[3-(2,3-dimethylphenoxy)-2-hydroxypropyl]-1,4,5,6,7,8-hexahydro-5-oxo-4-(2,3,5,6-tetrafluorophenyl)-1,7-naphthyridine-3-carboxylic acid methyl ester or a pharmaceutically acceptable salt thereof.

6. A compound of claim 2 which is 4-(2,3-dichloro-6-fluorophenyl)-7-[3-(2,3-dimethylphenoxy)-2-hydroxypropyl]-1,4,5,6,7,8-hexahydro-2-methyl-5-oxo-1,7-naphthyridine-3-carboxylic acid methyl ester or a pharmaceutically acceptable salt thereof.

7. A compound of claim 1 which is 7-[3-(2,3-dichlorophenoxy)-2-hydroxypropyl]-1,4,5,6,7,8-hexahydro-2-methyl-4-(2-methylphenyl)-5-oxo-1,7-naphthyridine-3-carboxylic acid methyl ester or a pharmaceutically acceptable salt thereof.

8. A compound of claim 2 which is 1,4,5,6,7,8-hexahydro-2-methyl-5-oxo-4-(pentafluorophenyl)-7-(3-phenoxy-2-hydroxypropyl)-1,7-naphthyridine-3-carboxylic acid methyl ester or a pharmaceutically acceptable salt thereof.

9. A compound of claim 2 which is 1,4,5,6,7,8-hexahydro-7-[3-(4-methoxyphenoxy)-2-hydroxypropyl]-2-methyl-5-oxo-4-(pentafluorophenyl)-1,7-naphthyridine-3-carboxylic acid methyl ester or a pharmaceutically acceptable salt thereof.

10. A compound of claim 2 which is 4-(2,3-dichlorophenyl)-7-[3-(2,3dimethylphenoxy)-2-hydroxypropyl]-1,4,5,6,7,8-hexahydro-2-methyl-5-oxo-1,7-naphthyridine-3-carboxylic acid methyl ester or a pharmaceutically acceptable salt thereof.

11. A compound of claim 1 which is 1,4,5,6,7,8-hexahydro-2-methyl-5-oxo-4-(pentafluorophenyl)-7-(3-phenoxypropyl)-1,7-naphthyridine-3-carboxylic acid methyl ester or a pharmaceutically acceptable salt thereof.

12. A compound of claim 2 which is 1,4,5,6,7,8-hexahydro-7-(2-hydroxy4-phenylbutyl)-2-methyl-5-oxo-4-(pentafluorophenyl)-1,7-naphthyridine-3-carboxylic acid methyl ester or a pharmaceutically acceptable salt thereof.

13. A compound of claim 1 which is 1,4,5,6,7,8-hexahydro-7-(2-hydroxy2-phenylethyl)-2-methyl-5-oxo-4-pentafluorophenyl-1,7-naphthyridine-3-carboxylic acid methyl ester or a pharmaceutically acceptable salt thereof.

* * * * *